United States Patent
Shim et al.

(10) Patent No.: US 9,465,007 B2
(45) Date of Patent: Oct. 11, 2016

(54) NANOSENSOR AND METHOD OF MANUFACTURING SAME

(71) Applicants: Jeo-young Shim, Yongin-si (KR);
Tae-han Jeon, Hwaseong-si (KR);
Dong-ho Lee, Seongnam-si (KR);
Hee-jeong Jeong, Suwon-si (KR);
Seong-ho Cho, Gwacheon-si (KR)

(72) Inventors: Jeo-young Shim, Yongin-si (KR);
Tae-han Jeon, Hwaseong-si (KR);
Dong-ho Lee, Seongnam-si (KR);
Hee-jeong Jeong, Suwon-si (KR);
Seong-ho Cho, Gwacheon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 178 days.

(21) Appl. No.: 14/224,770

(22) Filed: Mar. 25, 2014

(65) Prior Publication Data

US 2014/0202866 A1    Jul. 24, 2014

Related U.S. Application Data

(62) Division of application No. 13/410,883, filed on Mar. 2, 2012, now abandoned.

(30) Foreign Application Priority Data

Jun. 22, 2011 (KR) .................. 10-2011-0060796

(51) Int. Cl.
*G01N 27/447* (2006.01)
*G01N 33/487* (2006.01)

(52) U.S. Cl.
CPC .. *G01N 27/44791* (2013.01); *G01N 33/48721* (2013.01)

(58) Field of Classification Search
CPC ............. G01N 33/48721; G01N 27/44791; G01N 27/4473; B82Y 5/00; B82Y 15/00; Y10S 977/852; Y10S 977/733; Y10S 977/72; Y10S 977/721

See application file for complete search history.

(56) References Cited

U.S. PATENT DOCUMENTS 6,905,586 B2   6/2005   Lee et al.
7,258,838 B2   8/2007   Li et al.
(Continued)

FOREIGN PATENT DOCUMENTS

JP   2005-0229017 A   8/2005
KR   10-0451084 B1    9/2004
(Continued)

OTHER PUBLICATIONS

Felten et al., "Effect of oxygen rf-plasma on electronic properties of CNTs," *J. Phys. D: Appl. Phys.*, 2007, 40, pp. 7379-7382.

*Primary Examiner* — Luan Van
*Assistant Examiner* — Maris R Kessel
(74) *Attorney, Agent, or Firm* — Leydig, Voit & Mayer, Ltd.

(57) ABSTRACT

A nanosensor may include a substrate that has a hole formed therein, a first insulating layer that is disposed on the substrate and has a nanopore formed therein, first and second electrodes that are disposed on the first insulating layer and are spaced apart from each other, first and second electrode pads that are disposed on the first and second electrodes, respectively, and a protective layer disposed on the first and second electrode pads. A method of manufacturing a nanosensor may include forming a first insulating layer, graphene, and a metal layer on a substrate, patterning the metal layer and the graphene, forming a protective layer on a portion of the graphene and the metal layer, exposing a portion of the graphene by removing a portion of the protective layer, forming a hole in the substrate, and forming a nanopore in the first insulating layer and the graphene to be connected to the hole.

5 Claims, 13 Drawing Sheets

(56) References Cited

U.S. PATENT DOCUMENTS

| | | |
|---|---|---|
| 7,582,490 B2 | 9/2009 | Golovchenko et al. |
| 2008/0171316 A1* | 7/2008 | Golovchenko ...... C12Q 1/6869 435/6.11 |
| 2010/0140723 A1 | 6/2010 | Kurtz et al. |
| 2012/0037919 A1* | 2/2012 | Xu .......................... B82Y 15/00 257/76 |

FOREIGN PATENT DOCUMENTS

| | | |
|---|---|---|
| KR | 10-0801497 B1 | 1/2008 |
| KR | 20100028994 A | 3/2010 |
| KR | 20100082512 A | 7/2010 |
| KR | 10-1027074 B1 | 3/2011 |
| WO | WO 2010113090 A1 * | 10/2010 |

\* cited by examiner

NANOSENSOR AND METHOD OF MANUFACTURING SAME

CROSS-REFERENCE TO RELATED APPLICATION

This application is a divisional of U.S. patent application Ser. No. 13/410,883 filed Mar. 2, 2012, which claims priority to Korean Patent Application No. 10-2011-0060796, filed on Jun. 22, 2011, the entire disclosures of which are hereby incorporated by reference.

BACKGROUND

A Maxam-Gilbert method and a Sanger method are used to determine the order of bases of deoxyribonucleic acid (DNA). The Maxam-Gilbert method is a method of determining the order of bases of DNA by randomly performing cleavage at specific bases and separating DNA strands having different lengths by using electrophoresis. The Sanger method is a method of determining the order of bases of DNA by synthesizing a complementary DNA by putting a template DNA, a DNA polymerase, a primer, a normal deoxynucleotide triphosphate (dNTP), and a dideoxynucleotide triphosphate (ddNTP) into a tube. When the ddNTP is added while the complementary DNA is synthesized, DNA synthesis is terminated, to obtain complementary DNAs having different lengths, so that the order of bases of DNA may be determined by separating the complementary DNAs having different lengths by using electrophoresis. However, such methods used to determine the order of bases of DNA are time and effort-consuming. Accordingly, studies on a new next generation DNA sequencing method for determining the order of bases of DNA have recently been actively conducted.

SUMMARY

Additional aspects will be set forth in part in the description which follows and, in part, will be apparent from the description, or may be learned by practice of the presented embodiments.

According to an aspect of the present invention, a nanosensor includes: a substrate that has a hole formed therein; a first insulating layer that is disposed on the substrate and has a first nanopore formed therein to correspond to the hole; first and second electrodes that are disposed on the first insulating layer and are spaced apart from each other with the first nanopore therebetween; first and second electrode pads that are respectively disposed on the first and second electrodes; and a protective layer that is disposed on the first and second electrode pads.

The protective layer may cover portions of the first and second electrode pads, and expose portions of the first and second electrodes.

The nanosensor may further include a second insulating layer that is disposed on the protective layer and has a second nanopore formed therein to be connected to the first nanopore.

The second insulating layer may cover exposed portions of the first and second electrodes and the protective layer The first and second electrodes may include graphene or carbon nanotubes.

At least one of the first insulating layer and the second insulating layer may include a nitride.

The protective layer may include an oxide.

According to another aspect of the present invention, a method of manufacturing a nanosensor includes: forming a first insulating layer on one surface of a substrate; forming graphene on the first insulating layer; forming a metal layer on the graphene, and patterning the metal layer and the graphene; exposing a portion of the graphene by patterning the metal layer; forming a protective layer on the exposed portion of the graphene and the metal layer; exposing a portion of the graphene by removing a portion of the protective layer; and forming a hole in the substrate and forming a first nanopore in the first insulating layer and the graphene to be connected to the hole.

The forming of the graphene on the first insulating layer may include forming a catalyst layer on the first insulating layer and growing graphene on the catalyst layer.

The method may further include forming a second insulating layer on the exposed portion of the graphene and the protective layer.

The method may further include forming a second nanopore in the second insulating layer to be connected to the first nanopore.

The first and second nanopores may be simultaneously formed.

The metal layer and the graphene may be patterned into bow tie shapes.

The method may further include exposing a portion of the metal layer by etching a portion of the second insulating layer and the protective layer.

At least one of the first insulating layer, the second insulating layer, and the protective layer may be formed by using low-pressure chemical vapor deposition (LPCVD).

At least one of the first insulating layer and the second insulating layer may be formed at a temperature of 500° C. to 1000° C.

The protective layer may be formed at a temperature of 300° C. to 500° C.

According to another aspect of the present invention, a method of manufacturing a nanosensor includes: forming a first insulating layer on one surface of a substrate; forming graphene on the first insulating layer and patterning the graphene; forming a sacrificial layer on the graphene, and exposing a portion of the graphene by patterning the sacrificial layer; forming a second insulating layer on the exposed portion of the graphene and the patterned sacrificial layer; forming a photoresist layer on a portion of the second insulating layer and removing a remaining portion of the second insulating layer; exposing a remaining portion of the graphene by removing the patterned sacrificial layer; forming a metal layer on the photoresist layer and the exposed remaining portion of the graphene and removing the photoresist layer; and forming a hole in the substrate, and forming a nanopore in the first insulating layer, the graphene, and the second insulating layer to be connected to the hole.

The forming of the graphene on the first insulating layer may include transferring graphene grown on an auxiliary substrate from the auxiliary substrate to the first insulating layer.

The metal layer and the graphene may be patterned into bow tie shapes.

At least one of the first insulating layer and the second insulating layer may include a nitride.

The sacrificial layer may include an oxide.

At least one of the first insulating layer, the second insulating layer, and the sacrificial layer may be formed by using LPCVD.

At least one of the first insulating layer and the second insulating layer may be formed at a temperature of 500° C. to 1000° C.

The sacrificial layer may be formed at a temperature of 300° C. to 500° C.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
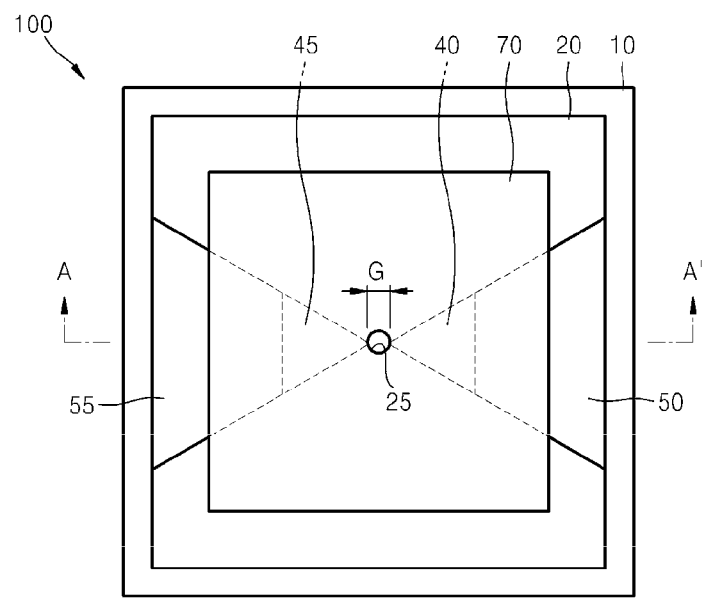
FIG. 1A is a plan view of a nanosensor according to an embodiment of the present invention.

Various exemplary embodiments will now be described more fully with reference to the accompanying drawings in which some exemplary embodiments are shown.

Detailed illustrative exemplary embodiments are disclosed herein. However, specific structural and functional details disclosed herein are merely representative for purposes of describing exemplary embodiments. This invention may, however, may be embodied in many alternate forms and should not be construed as limited to only the exemplary embodiments set forth herein.

Accordingly, while exemplary embodiments are capable of various modifications and alternative forms, embodiments thereof are shown by way of example in the drawings and will herein be described in detail. It should be understood, however, that there is no intent to limit exemplary embodiments to the particular forms disclosed, but on the contrary, exemplary embodiments are to cover all modifications, equivalents, and alternatives falling within the scope of the invention. Like numbers refer to like elements throughout the description of the figures.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of exemplary embodiments. As used herein, the term "and/or" includes any and all combinations of one or more of the associated listed items.

It will be understood that when an element or layer is referred to as being "formed on" another element or layer, it may be directly or indirectly formed on the other element or layer. In other words, for example, intervening elements or layers may be present. In contrast, when an element or layer is referred to as being "directly formed on" another element, there are no intervening elements or layers present. Other words used to describe the relationship between elements or layers should be interpreted in a like fashion (e.g., "between" versus "directly between", "adjacent" versus "directly adjacent", etc.).

The terminology used herein is for the purpose of describing particular embodiments only and is not intended to be limiting of exemplary embodiments. As used herein, the singular forms "a", "an", and "the" are intended to include the plural forms as well, unless the context clearly indicates otherwise. It will be further understood that the terms "comprises", "comprising", "includes", and/or "including" when used herein, specify the presence of stated features, integers, steps, operations, elements, and/or components, but do not preclude the presence or addition of one or more other features, integers, steps, operations, elements, components, and/or groups thereof.

In the drawings, the thicknesses of layers and regions are exaggerated for clarity. Like reference numerals in the drawings denote like elements.

The present invention will now be described more fully with reference to the accompanying drawings, in which exemplary embodiments of the invention are shown. In the drawings, the same elements having the same configurations are denoted by the same reference numerals. Sizes of elements in the drawings may be exaggerated for clarity and convenience.

Figure 1B:
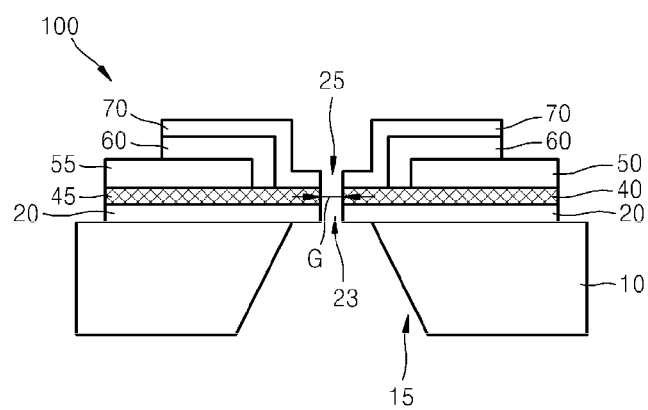
FIG. 1B is a cross-sectional view taken along line A-A' of the nanosensor of FIG. 1A.
Figure 1C:
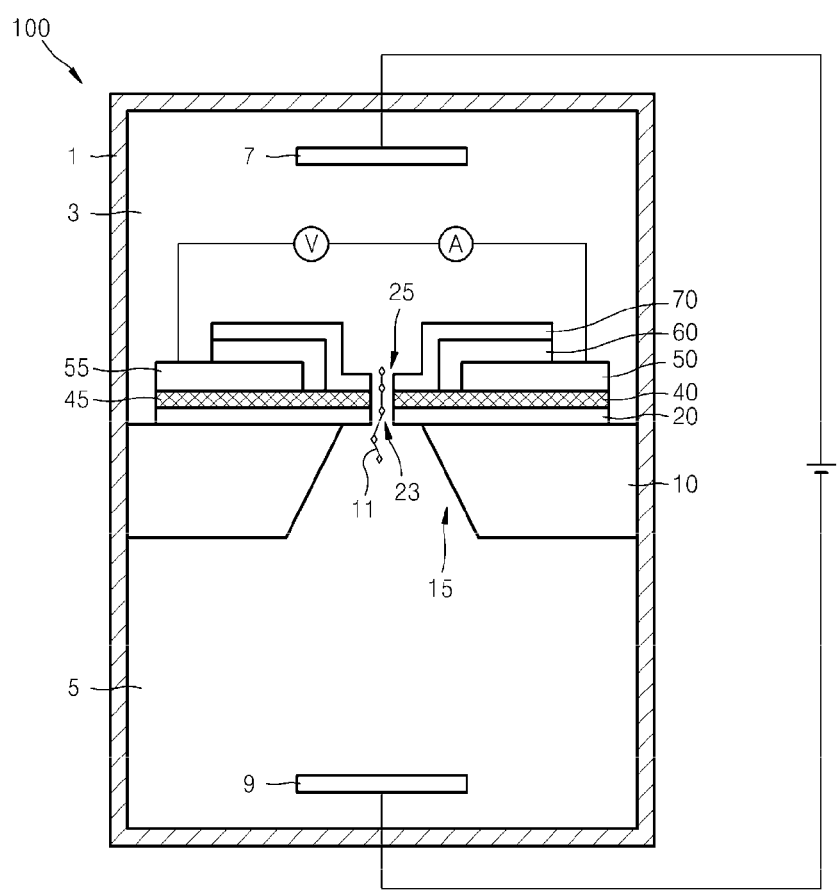
FIG. 1C is a cross-sectional view for explaining an operation of the nanosensor of FIG. 1A.

FIG. 1A is a plan view of a nanosensor 100 according to an embodiment of the present invention. FIG. 1B is a cross-sectional view taken along line A-A' of the nanosensor 100 of FIG. 1A. FIG. 1C is a cross-sectional view for explaining an operation of the nanosensor 100 of FIG. 1A.

Referring to FIGS. 1A and 1B, the nanosensor 100 may include a first insulating layer 20 disposed on a substrate 10, first and second electrodes 40 and 45 disposed on the first insulating layer 20, first and second electrode pads 50 and 55 disposed on the first and second electrodes 40 and 45, respectively, and a protective layer 60 disposed on the first and second electrode pads 50 and 55. The nanosensor 100 may further include a second insulating layer 70 disposed on the protective layer 60.

The substrate 10 may support the first insulating layer 20 disposed on a top surface of the substrate 10, the first and second electrodes 40 and 45, the first and second electrode pads 50 and 55, the protective layer 60, and the second insulating layer 70. The substrate 10 may be formed of one or more of a semiconductor material, a polymer material, or the like. Examples of the semiconductor material may include, for example, silicon (Si), germanium (Ge), gallium arsenide (GaAs), gallium nitride (GaN), combinations thereof, and so on, and examples of the polymer material may include an organic polymer and an inorganic polymer. Alternatively, the substrate 10 may be formed of quartz, glass, or the like. A thickness of the substrate 10 may range from tens of micrometers (μm) to hundreds of μm. For example, a thickness of the substrate 10 may range from about 10 μm to about 500 μm, and more specifically, may range from about 200 μm to about 400 μm.

A hole 15 may be formed in the substrate 10. A "hole" as used herein refers to a passageway through the thickness of a substrate (or other layers of material), which is defined by openings in each of two opposing and substantially parallel surfaces of the substrate or layer, which openings extend through the thickness of the substrate or layer and are connected to form the passageway. The hole 15 may be formed by using wet etching, for example, buffered oxide etching (BOE) using potassium hydroxide (KOH), or the like. A diameter of the hole 15 may be equal to or less than hundreds of μm (e.g., less than about 900 μm, less than about 800 µm, less than about 700 µm, less than about 600 µm, or less than about 500 µm. For example, a diameter of the hole 15 may range from about 30 µm to about 490 µm, and more specifically, from about 60 µm to about 460 µm. The hole 15 may be formed by using selective etching, and may become narrower from a bottom surface of the substrate 10 toward the top surface of the substrate 10 on which the first insulating layer 20 is disposed. In other words, the hole 15 may be formed to have a tapered shape that becomes narrower along a path from a lower portion of the substrate (i.e., furthest from the face of the substrate upon which the insulating and electrode layers are to be disposed) toward an upper portion of the substrate 10 (i.e., closest to the face of the substrate upon which the insulating and electrode layers are to be disposed). In other words, the dimension (e.g., diameter) of the hole at the upper portion (upper face) of the substrate is smaller than the dimension of the hole at the lower portion (lower face) of the substrate.

The first insulating layer 20 may be disposed on the substrate 10 to cover the hole 15. The first insulating layer 20 may be formed of an insulating material. The first insulating layer 20 may be formed of a nitride, for example, silicon nitride ($Si_xN_y$). The first insulating layer 20 may be formed as a thin film having a thickness equal to or less than tens of nanometers (nm). In other words, a thickness of the first insulating layer 20 may range from about 10 nm to about 100 nm. If the first insulating layer 20 is formed of a nitride, a nanopore as explained below may be easily formed.

A first nanopore 23 may be formed in the first insulating layer 20. The first nanopore 23 may be connected to the hole 15 formed in the substrate 10. In other words, the first nanopore 23 may be formed in an area corresponding to the hole 15. A size (e.g., diameter) of the first nanopore 23 may be determined according to a size of a target molecule to be detected or sequenced. A diameter of the first nanopore 23 may range from several nm to tens of nm. For example, a diameter of the first nanopore 23 may range from about 1 nm to about 100 nm, and more specifically, from about 2 nm to about 10 nm. The first nanopore 23 may be formed by using, for example, a transmission electron microscope (TEM), a scanning electron microscope (SEM), or the like. More specifically, the first nanopore 23 may be formed by using an electron beam, a focused ion beam, a neutron beam, an X-ray, a y-ray, or the like.

The first and second electrodes 40 and 45 may be disposed on the first insulating layer 20. The first and second electrodes 40 and 45 may be spaced apart from each other with the first nanopore 23 positioned therebetween. The first and second electrodes 40 and 45 may be symmetrical about the first nanopore 23, and a nanogap G may be formed between the first and second electrodes 40 and 45 by the spacing of the electrodes relative to one another (e.g., the electrodes are spaced apart from one another by a distance that defines the nanogap G). A size of the nanogap G may be equal to or less than about 100 nm, for example, equal to or greater than a size of a target molecule passing through the first nanopore 23. A size of the nanogap G may range from, for example, about 1.2 nm to about 100 nm, from about 2.2 nm to about 100 nm, from about 5 nm to about 100 nm, from about 10 nm to about 100 nm, from about 15 nm to about 100 nm, from about 20 nm to about 100 nm, from about 30 nm to about 100 nm, from about 40 nm to about 100 nm, from about 50 nm to about 100 nm, or from about 70 nm to about 100 nm. Also, a size of the nanogap G may range from about 1.2 nm to about 90 nm, from about 2.2 nm to about 90 nm, from about 5 nm to about 90 nm, from about 10 nm to about 80 nm, from about 15 nm to about 70 nm, from about 20 nm to about 60 nm, from about 30 nm to about 50 nm, from about 40 nm to about 50 nm, from about 5 nm to about 80 nm, or from about 10 nm to about 60 nm. Also, a size of the nanogap G may be equal to or greater than a diameter of the first nanopore 23.

The first and second electrodes 40 and 45 may have polygonal shapes such as triangular shapes, as shown in FIG. 1A. However, the present embodiment is not limited thereto, and the first and second electrodes 40 and 45 may have other various shapes. Ends of the first and second electrodes 40 and 45 which face each other to form the nanogap G may have a shape that tapers towards the nanogap G, such that the portion of the electrode adjacent to and defining the boundary of the nanogap G has a small dimension.

Each of the first and second electrodes 40 and 45 may comprise a conductive material, for example, copper (Cu), aluminum (Al), gold (Au), silver (Ag), chromium (Cr), or a mixture thereof. Alternatively, or in addition, Each of the first and second electrodes 40 and 45 may be formed of or comprise graphene or carbon nanotubes (CNTs). For instance, each of the first and second electrodes 40 and 45 may have a structure including one graphene sheet or a plurality of stacked graphene sheets.

Graphene is an allotrope of carbon, of which a structure is one-atom-thick planar sheet of $sp^2$-bonded carbon atoms that are densely packed in a honeycomb crystal lattice. Graphene is a conductive material and a single graphene layer has a thickness of, for example, about 0.34 nm. Graphene, which is structurally and chemically stable and an excellent conductor, has higher charge mobility than silicon (Si) and may enable more current to flow than copper. CNTs are allotropes of carbon with a cylindrical nanostructure. The chemical bonding of CNTs is composed of $sp^2$ bonds, similar to those of graphite.

A thickness of each of the first and second electrodes 40 and 45 may be equal to or less than about 3.4 nm, and more specifically, equal to or less than about 1 nm. If each of the first and second electrodes 40 and 45 is formed of graphene, each of the first and second electrodes 40 and 45 more accurately distinguishes a target molecule because each of the first and second electrodes 40 and 45 has higher conductivity than a metal electrode and has a low thickness. In particular, a thickness of one graphene sheet is similar to a size of one base constituting DNA. Each of the first and second electrodes 40 and 45 may be formed of a conductive material. Each of the first and second electrodes 40 and 45 may be formed of, for example, copper (Cu), aluminum (Al), gold (Au), silver (Ag), chromium (Cr), or a mixture thereof.

The first and second electrode pads 50 and 55 may be disposed on the first and second electrodes 40 and 45, respectively. The first and second electrode pads 50 and 55 may have polygonal shapes such as quadrangular shapes as shown in FIG. 1A. However, the present embodiment is not limited thereto, and the first and second electrode pads 50 and 55 may have other various shapes. The first and second electrode pads 50 and 55 may be spaced apart from each other providing a gap greater in size than the nanogap G formed by the first and second electrodes 40 and 45. In other words, the nanogap G is positioned within the gap defined by the distance between the first and second electrode pads. However, in order to efficiently apply a voltage or current from an external power source to the first and second electrodes 40 and 45, a contact area between the first and second electrode pads 50 and 55 and the first and second electrodes 40 and 45 may be maximized. Each of the first and second electrode pads 50 and 55 may be formed of a conductive material, for example, gold (Au), chromium (Cr), copper (Cu), nickel (Ni), cobalt (Co), iron (Fe), silver (Ag), aluminum (Al), titanium (Ti), palladium (Pd), or a mixture thereof.

The protective layer 60 may be disposed on the first and second electrode pads 50 and 55 to partially cover the first and second electrode pads 50 and 55. The protective layer 60 may expose edge portions of the first and second electrode pads 50 and 55, particularly those edge portions that are furthest from the first nanopore 23. The protective layer 60 may partially contact (partially cover) the first and second electrodes 40 and 45, without covering and, thus, leaving exposed those portions of the first and second electrodes 40 and 45 adjacent to the first nanopore 23 and defining the nanogap G.

The protective layer 60 may protect the first and second electrode pads 50 and 55 from a high temperature process. Since each of the first and second electrode pads 50 and 55 is formed of a metal, each of the first and second electrode pads 50 and 55 may melt in a high temperature process. The protective layer 60 may prevent heat of a high temperature process for forming the second insulating layer 70 thereon to be transferred to the first and second electrode pads 50 and 55. The protective layer 60 may be formed of an oxide, for example, a material selected from the group consisting of $Si_xO_y$, $Al_2O_3$, $TiO_2$, $BaTiO_3$, $PbTiO_3$, and a mixture thereof. A thickness of the protective layer 60 may range from about 10 nm to about 500 nm, and more specifically, from about 50 nm to about 200 nm.

The second insulating layer 70 may be further disposed on the protective layer 60. The second insulating layer 70 may cover the protective layer 60, and also may cover the exposed portions of the first and second electrodes 40 and 45. The "exposed" portions of the first and second electrodes are those portions of the first and second electrodes 40 and 45 adjacent to the nanogap G and nanopore that were not covered by the protective layer. The second insulating layer 70 may insulate the first and second electrodes 40 and 45 by covering the exposed portions of the first and second electrodes 40 and 45. The second insulating layer 70 may be formed of a nitride, for example, $Si_xN_y$. The second insulating layer 70 may be formed as a thin film having a thickness equal to or less than about tens of nm. In other words, a thickness of the second insulating layer 70 may range from about 10 nm to about 100 nm.

A second nanopore 25 may be formed in the second insulating layer 70, and the second nanopore 25 may be connected to the first nanopore 23 formed in the first insulating layer 20. In other words, the first and second nanopores 23 and 25 may together form one continuous nanopore. The sizes (diameters) of the first and second nanopores 23 and 25 may be the same. Also, the first and second nanopores 23 and 25 may be simultaneously formed in the first and second insulating layers 20 and 70, respectively. If the second insulating layer 70 is formed of a nitride, the second nanopore 25 may be easily formed.

Referring to FIG. 1C, the nanosensor 100 may further include a housing 1 surrounding the substrate and any associated layers or other elements. The housing 1 may be divided into two regions about the substrate 10. In other words, the housing 1 may include a first region 3 above the substrate 10 and a second region 5 below the substrate 10. The first region 3 and the second region 5 may be connected to each other through the first and second nanopores 23 and 25. Upper and lower electrodes 7 and 9 may be respectively disposed in the first and second regions 3 and 5. A voltage may be applied to the upper and lower electrodes 7 and 9 from an external power source. The upper electrode 7 may be a positive (+) electrode and the lower electrode 9 may be a negative (−) electrode, or vice versa. The housing 1 may be filled with a buffer solution such as water, deionized water, or an electrolyte solution. The buffer solution may be a medium through which a target molecule moves. The terms "above" and "below" are used arbitrarily to refer to distinguishing between various elements positioned relative to one another, and does not imply any particular orientation of the device when in use.

A target molecule may be introduced into the second region 5 from the outside the housing. The target molecule may be an object to be detected or sequenced. Examples of the target molecule may include a nucleic acid, a protein, or a sugar. More specifically, examples of the target molecule may include a single-stranded DNA, a double-stranded DNA, a ribonucleic acid (RNA), a peptide nucleic acid (PNA), and a polypeptide.

A single-stranded DNA 11 is illustrated as a target molecule in FIG. 1C. Since a surface of the DNA 11 is negatively charged, the DNA 11 may move from the second region 5 in which the lower electrode 9 which is a negative electrode is disposed to the first region 3 in which the upper electrode 7 which is a positive electrode is disposed. In other words, the DNA 11 introduced into the second region 5 may move to a place close to the hole 15 of the substrate 10 due to an electric field applied to the DNA 11. The DNA 11 may be guided by the hole 15 to the first nanopore 23.

The nanosensor 100 may detect or distinguish a target molecule by measuring a change in an electrical signal between the first and second electrodes 40 and 45 when the target molecule passes through the first and second nanopores 23 and 25 and into or through the nanogap G. In other words, the nanosensor 100 measures a change in an electrical signal in the nanogap G due to the passing of the target molecule therethrough. A device for measuring an electrical signal, for example, an ammeter or a voltmeter, may be connected to the first and second electrodes 40 and 45 to measure a change in an electrical signal in the nanogap G.

The nanosensor 100 may detect each of the monomers of a polymeric target molecule (e.g., DNA, RNA, etc). In detail, the nanosensor 100 may electrically detect each of the nucleotides constituting a nucleic acid. For example, a base may be distinguished by applying a bias voltage to the first and second electrodes 40 and 45 and measuring a change in a tunneling current between the first and second electrodes 40 and 45 when the DNA 11 passes through the nanogap G. In other words, the base may be distinguished by measuring a change in a tunneling current between the nanogap G when the base constituting the single-stranded DNA 11 passes through the nanogap G. However, a measured electrical signal is not limited thereto, and a blockade current instead of a tunneling current may be used.

The nanosensor 100 may rapidly and accurately determine the order of bases of DNA by using a next generation sequencing method without randomly cutting the single-stranded DNA 11 or without performing synthesis and electrophoresis on complementary DNAs, thereby reducing costs.

Figure 2:
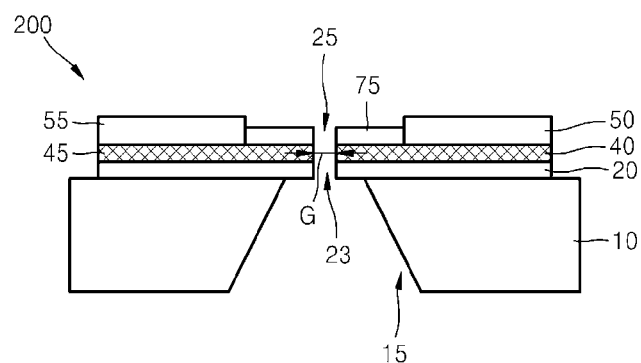
FIG. 2 is a cross-sectional view of a nanosensor according to another embodiment of the present invention.

FIG. 2 is a cross-sectional view of a nanosensor 200 according to another embodiment of the present invention. The following explanation will be made by focusing on a difference between the nanosensor 100 of FIG. 1 and the nanosensor 200 of FIG. 2.

Referring to FIG. 2, the nanosensor 200 may include the first insulating layer 20 disposed on the substrate 10, the first and second electrodes 40 and 45 disposed on the first insulating layer 20, the first and second electrode pads 50 and 55 disposed on the first and second electrodes 40 and 45, respectively, and a second insulating layer 75 disposed on the first and second electrodes 40 and 45.

The first and second electrode pads 50 and 55 may be disposed on the first and second electrodes 40 and 45, respectively. The first and second electrode pads 50 and 55 may be spaced apart from each other to have the second insulating layer 75 therebetween. The first and second electrode pads 50 and 55 may be disposed on edge portions of the first and second electrodes 40 and 45, respectively. Each of the first and second electrode pads 50 and 55 may be formed of a conductive material, for example, Cu, Al, Au, Ag, Cr, or a mixture thereof.

The second insulating layer 75 may be disposed on the first and second electrodes 40 and 45. The second insulating layer 75 may insulate the first and second electrodes 40 and 45 by covering exposed portions of the first and second electrodes 40 and 45. The second insulating layer 75 may be formed of a nitride, for example, $Si_xN_y$. Both sides of the second insulating layer 75 contact the first and second electrode pads 50 and 55, respectively. The second insulating layer 75 may be formed as a thin film having a thickness equal to or less than about tens of nm. In other words, a thickness of the second insulating layer 75 may range from about 10 nm to about 100 nm. The second nanopore 25 may be formed in the second insulating layer 75, and the second nanopore 25 may be connected to the first nanopore 23 formed in the first insulating layer 20. In other words, the first and second nanopores 23 and 25 may form one nanopore, and sizes of the first and second nanopores 23 and 25 may be the same. Also, the first and second nanopores 23 and 25 may be simultaneously formed in the first and second insulating layers 20 and 75, respectively. If each of the first and second insulating layers 20 and 75 are formed of a nitride, the first and second nanopores 23 and 25 may be easily formed.

Since the second insulating layer 75 is formed in a high temperature process, the second insulating layer 75 may be formed earlier than the first and second electrode pads 50 and 55 that are each formed of a metal and thus may melt at a high temperature. For example, the second insulating layer 75 and the first and second electrode pads 50 and 55 may be formed on the first and second electrodes 40 and 45 by using a sacrificial layer. The sacrificial layer may be formed of an oxide, for example, a material selected from the group consisting of $Si_xO_y$, $Al_2O_3$, $TiO_2$, $BaTiO_3$, $PbTiO_3$, and a mixture thereof, which will be explained in detail with reference to a method of manufacturing the nanosensor 200.

FIGS. 3A through 3M are cross-sectional views illustrating a method of manufacturing the nanosensor 100 of FIG. 1A, according to an embodiment of the present invention.

Figure 3A:
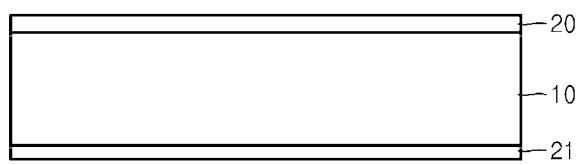
FIGS. 3A through 3M are cross-sectional views illustrating a method of manufacturing the nanosensor of FIG. 1A, according to an embodiment of the present invention.

Referring to FIG. 3A, the substrate 10 may be prepared, and the first insulating layer 20 may be formed on the substrate 10. The substrate 10 may be formed of a semiconductor material, a polymer material, or the like. Examples of the semiconductor material may include, for example, Si, Ge, GaAs, and GaN, and examples of the polymer material may include an organic polymer and an inorganic polymer. Alternatively, the substrate 10 may be formed of quartz, glass, or the like. A thickness of the substrate 10 may range from tens of μm to hundreds of μm. For example, a thickness of the substrate 10 may range from about 10 μm to about 500 μm, and more specifically, from about 200 μm to about 400 μm.

The first insulating layer 20 may be formed by depositing a nitride, for example, $Si_xN_y$, on the substrate 10. The first insulating layer 20 may be formed as a thin film or a thin layer, and a thickness of the first insulating layer 20 may be equal to or less than about tens of nm. In other words, a thickness of the first insulating layer 20 may range from about 10 nm to about 100 nm. The first insulating layer 20 may be formed by using, for example, low-pressure chemical vapor deposition (LPCVD), plasma-enhanced chemical vapor deposition (PECVD), or the like. If the first insulating layer 20 is formed by using LPCVD, a first insulating layer 21 may also be formed on a bottom surface of the substrate 10, and the first insulating layer 21 formed on the bottom surface of the substrate 10 is not shown in the remaining drawings.

Figure 3B:
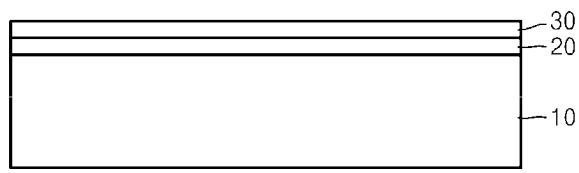

Referring to FIG. 3B, a catalyst layer 30 may be formed on the first insulating layer 20. The catalyst layer 30 may be formed of a metal, for example, Cu, Ni, Co, Fe, Au, Ag, Al, Ti, Pd, or a mixture thereof. Also, the catalyst layer 30 may have a structure in which the above metals may be stacked on one another. For example, the catalyst layer 30 may include a lower layer formed of Cu and an upper layer stacked on the lower layer and formed of Ni. The lower layer may be thicker than the upper layer. The lower layer may be formed to a thickness of hundreds of nm, and the upper layer may be formed to a thickness of tens of nm.

Figure 3C:
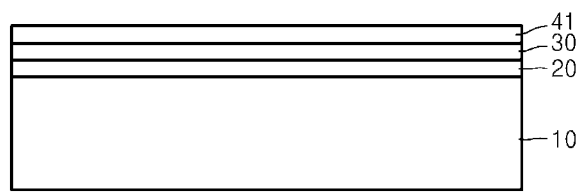

Referring to FIG. 3C, graphene 41 may be grown on the catalyst layer 30. The graphene 41 may be grown from the catalyst layer 30 by using chemical vapor deposition (CVD) or the like. The graphene 41 may include at least one graphene sheet. A thickness of the graphene 41 may be equal to or less than about 3.4 nm, and more specifically, may be equal to or less than about 1 nm. The graphene 41 may be formed by using mechanical or chemical exfoliation, epitaxial growth, or the like. Also, the graphene 41 may be grown on an auxiliary substrate and may be transferred from the auxiliary substrate to the insulating layer 20. If the catalyst layer 30 has a structure in which a plurality of metals are stacked, the graphene 41 may be grown on the catalyst layer 30 at a high temperature equal to or higher than about 1000° C., and the catalyst layer 30 may be a single layer formed of a mixture obtained by melting the plurality of metals.

Figure 3D:
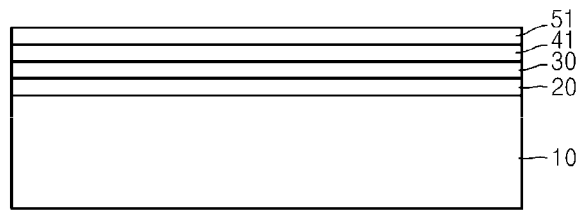

Referring to FIG. 3D, a metal layer 51 may be formed on the graphene 41. The metal layer 51 may be formed of a metal, for example, Au, Cr, Cu, Ni, Co, Fe, Ag, Al, Ti, Pd, or a mixture thereof. Also, the metal layer 51 may have a structure in which the above metals are stacked on one another. For example, the metal layer 51 may include a lower layer formed of Cr and an upper layer formed of Au that is stacked on the lower layer. The upper layer may be thicker than the lower layer. The upper layer may be formed to a thickness of hundreds of nm, and the lower layer may be formed to a thickness of tens of nm.

Figure 3E:
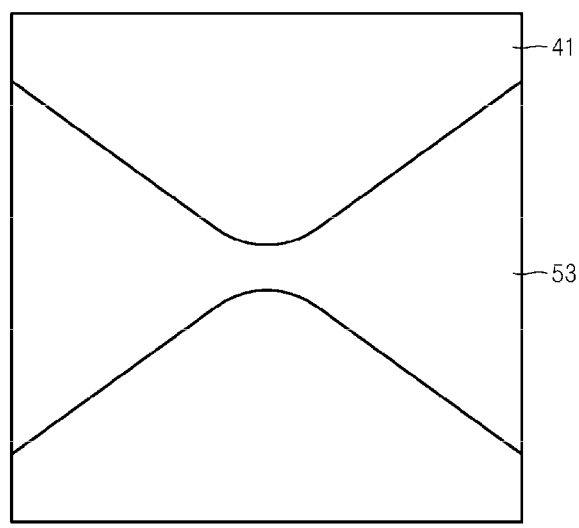

Referring to FIG. 3E, the metal layer 51 may be patterned. The metal layer 51 may be patterned by using photolithography and etching. For example, a photoresist layer may be disposed on the metal layer 51, and may be patterned. The metal layer 51 may be etched by using the photoresist layer as an etch mask. The metal layer 51 may be wet-etched to form an etched metal layer 53. A plane shape of the metal layer 53 may be a bow tie. The metal layer 53 may partially expose the graphene 41 disposed under the metal layer 53.

Figure 3F:
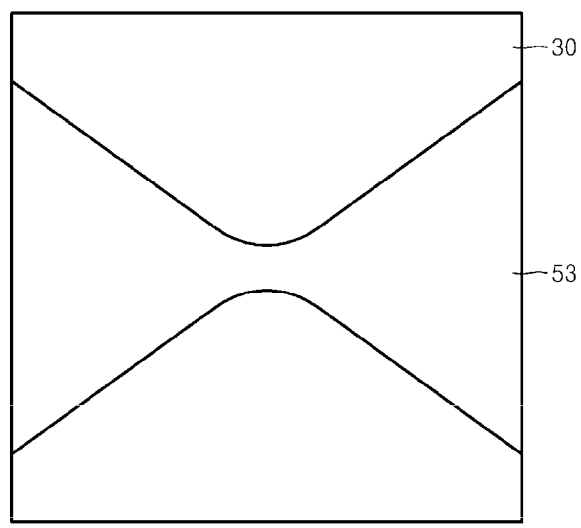

Referring to FIG. 3F, the graphene 41 (shown in FIG. 3E, not 3F) may be patterned. The graphene 41 may be patterned through the photoresist layer. The graphene 41 (shown in FIG. 3E, not 3F) may be etched by using oxygen plasma etching, to form an etched graphene 43. A plane shape of the graphene 43 may be a bow tie. The graphene 43 and the metal layer 53 may be patterned into the same shape by using the same photoresist layer. The graphene 43 may partially expose the catalyst layer 30 disposed under the graphene 43. The photoresist layer may be removed.

Figure 3G:
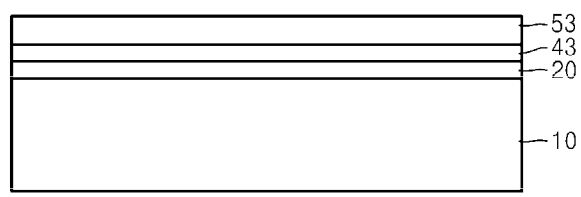

Referring to FIG. 3G, the catalyst layer 30 (shown in FIG. 3F, not 3G) may be removed. The catalyst layer 30 may be, for example, wet-etched and removed. If the catalyst layer 30 is etched, the graphene 43 may be disposed on the first insulating layer 20.

Figure 3H:
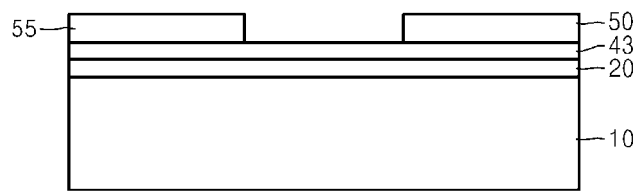

Referring to FIG. 3H, the metal layer 53 may be patterned again. A portion of the graphene 43 disposed under the metal layer 53 may be exposed by patterning the metal layer 53. A middle portion, that is, a thinnest portion, of the bow tie may be removed from the bow tie of the metal layer 53. The metal layer 53 may be patterned to form the first and second electrode pads 50 and 55 having quadrangular or trapezoidal shapes which are spaced apart from each other. Shapes of the first and second electrode pads 50 and 55 are not limited thereto, and may be other various shapes.

Figure 3I:
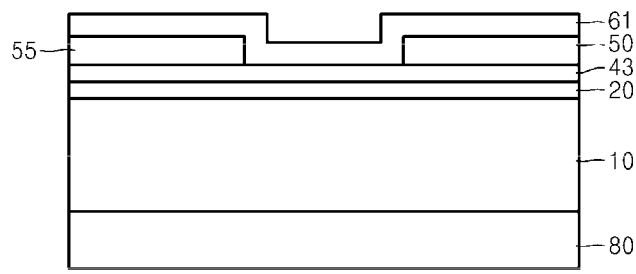

Referring to FIG. 3I, a protective layer 61 may be formed on the exposed portion of the graphene 43 and the first and second electrode pads 50 and 55. A mask layer 80 may be formed on the bottom surface of the substrate 10. The protective layer 61 may be formed of an oxide, for example, a material selected from the group consisting of $Si_xO_y$, $Al_2O_3$, $TiO_2$, $BaTiO_3$, $PbTiO_3$, and a mixture thereof. If the protective layer 61 is formed by using PECVD, the graphene 43 disposed under the protective layer 61 may be disadvantageously etched by plasma. Accordingly, the protective layer 61 may be formed by using LPCVD. Also, the protective layer 61 may be formed at a low temperature equal to or lower than about 500° C., for example, from about 100° C. to about 500° C., and more specifically, from about 300° C. to about 500° C., and thus the first and second electrode pads 50 and 55 may be prevented from melting during a high temperature process. In other words, the protective layer 61, which is a low temperature oxide layer, may be formed by using LPCVD at a low temperature equal to or lower than about 500° C., for example, from about 100° C. to about 500° C., and more specifically, from about 300° C. to about 500° C. A thickness of the protective layer 61 may range from about 10 nm to about 500 nm, and more specifically, from about 50 nm to about 200 nm. The mask layer 80 may be formed of a nitride, for example, $Si_xN_y$. The mask layer 80 may be formed to a thickness of hundreds of nm, for example, from about 100 nm to about 500 nm. For example, the mask layer 80 may be formed by depositing $Si_xN_y$ on the bottom surface of the substrate 10 by using PECVD.

Figure 3J:
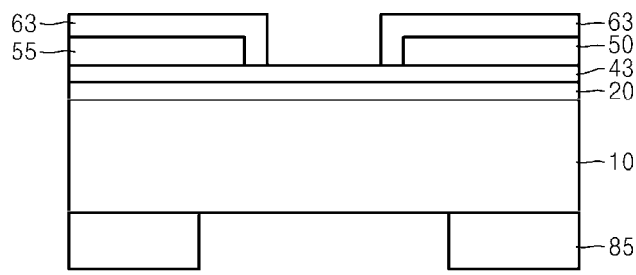

Referring to FIG. 3J, the protective layer 61 and the mask layer 80 may be patterned. First, a portion of the protective layer 61 may be removed to expose a portion of the graphene 43 disposed under the protective layer 61. A portion of the protective layer 61 directly disposed on the graphene 43 may be removed. A portion of the protective layer 61 may be removed by using wet etching, for example, BOE using a KOH solution. A protective layer 63 may expose a middle portion of a bow tie of the graphene 43. The mask layer 80 may be dry-etched to form a mask layer 85. The mask layer 80 may be etched by using, for example, reactive ion etching (RIE).

Figure 3K:
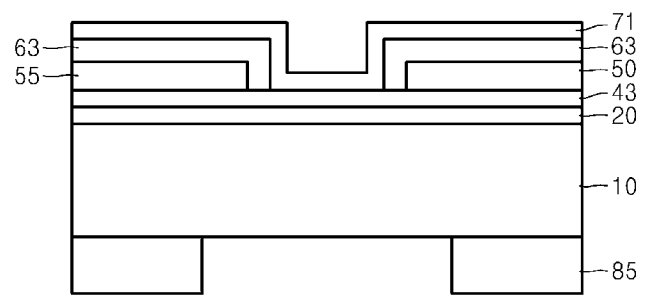

Referring to FIG. 3K, a second insulating layer 71 may be formed on the exposed portion of the graphene 43 and the protective layer 63. The second insulating layer 71 may be formed by depositing a nitride, for example, $Si_xN_y$, on the protective layer 63. The second insulating layer 71 may insulate the exposed portion of the graphene 43 by covering the exposed portion of the graphene 43. The second insulating layer 71 may be formed as a thin film or a thin layer, and a thickness of the second insulating layer 71 may be equal to or less than about tens of nm. In other words, a thickness of the second insulating layer 71 may range from about 10 nm to about 100 nm. If the second insulating layer 71 is also disposed on the exposed portion of the graphene 43 and is formed by using PECVD, the graphene 43 may be damaged. Accordingly, the second insulating layer 71 may be formed by using, for example, LPCVD. Also, the second insulating layer 71 may be formed by using LPCVD at a high temperature equal to or higher than about 500° C., for example, from about 500° C. to about 1000° C. If the second insulating layer 71 is formed at a high temperature, the protective layer 63 may protect the first and second electrode pads 50 and 55 from a high temperature process. In other words, the protective layer 63 prevents heat of a high temperature process from being transferred to the first and second electrode pads 50 and 55, thereby preventing the first and second electrode pads 50 and 55 each formed of a metal from melting.

Figure 3L:
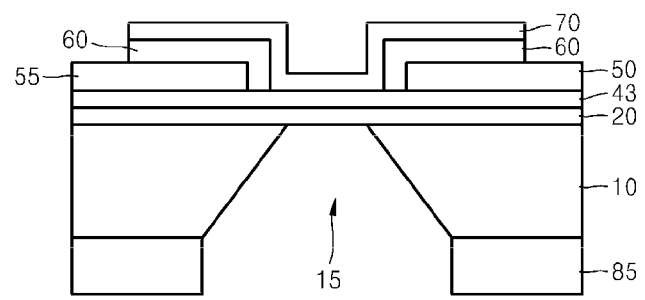

Referring to FIG. 3L, the hole 15 may be formed in the substrate 10 by removing edges of the protective layer 63 and the second insulating layer 71. The edge of the second insulating layer 71 may be removed by using dry etching, for example, RIE. Once the edge of the second insulating layer 71 is etched, the edge of the protective layer 63 disposed under the second insulating layer 71 may be exposed. The edge of the protective layer 63 may be removed by using wet etching, for example, BOE. Once the edge of the protective layer 63 is etched, portions of the first and second electrode pads 50 and 55 may be exposed. A voltage or current may be applied from the outside through the exposed portions of the first and second electrode pads 50 and 55.

The hole 15 may be formed by using wafer backside etching while shielding a front surface of the substrate 10. The hole 15 may be formed by using wet etching by using the mask layer 85 as a hard mask. The hole 15 may be formed by using, for example, KOH etching or the like. A diameter of the hole 15 may be equal to or less than tens of μm. For example, a diameter of the hole 15 may range from about 30 μm to about 490 μm, and more specifically, from about 60 μm to about 460 μm. The hole 15 may be formed by using selective etching, and may become narrower from the bottom surface of the substrate 10 toward the top surface of the substrate 10 on which the first insulating layer 20 is disposed. In other words, the hole 15 may have a tapered shape that becomes narrower from a lower portion toward an upper portion of the substrate 10.

Figure 3M:
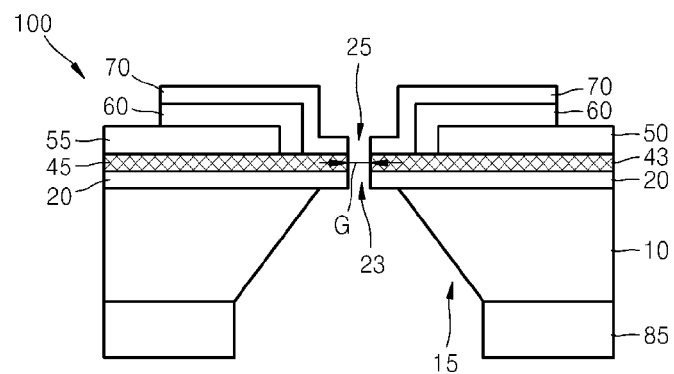

Referring to FIG. 3M, a nanopore may be formed in the first insulating layer 20, the graphene 43, and the second insulating layer 70. The nanopore may include the first nanopore 23 formed in the first insulating layer 20 and the second nanopore 25 formed in the second insulating layer 70. The first and second nanopores 23 and 25 may be simultaneously formed in the first insulating layer 20, the graphene 43, and the second insulating layer 70. Each of the first insulating layer 20 and the second insulating layer 70 may be formed of a nitride, and thus the first and second nanopores 23 and 25 may be easily formed. The first nanopore 23 may be connected to the hole 15 formed in the substrate 10. In other words, the first nanopore 23 may be formed in an area corresponding to the hole 15. A size of the first and second nanopores 23 and 25 may be determined according to a size of a target molecule to be detected or sequenced. A diameter of the first and second nanopores 23 and 25 may range from several nm to tens of nm. For example, a diameter of the first and second nanopores 23 and 25 may range from about 1 nm to about 100 nm, and more specifically, from about 2 nm to about 10 nm. The first and second nanopores 23 and 25 may be formed by using, for example, TEM, SEM, or the like. More specifically, the first and second nanopores 23 and 25 may be formed by using an electron beam, a focused ion beam, a neutron beam, an X-ray, a y-ray, or the like. The graphene 43 may be divided into the first and second electrodes 40 and 45 based on the nanopore formed in the graphene 43.

FIGS. 4A through 4L are cross-sectional views illustrating a method of manufacturing the nanosensor 200 of FIG. 2, according to an embodiment of the present invention.

Figure 4A:
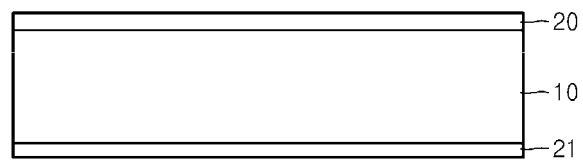
FIGS. 4A through 4L are cross-sectional views illustrating a method of manufacturing the nanosensor of FIG. 2, according to an embodiment of the present invention.

Referring to FIG. 4A, the substrate 10 may be prepared, and the first insulating layer 20 may be formed on the substrate 10. The substrate 10 may be formed of a semiconductor material, a polymer material, or the like. Examples of the semiconductor material may include, for example, Si, Ge, GaAs, and GaN, and examples of the polymer material may include an organic polymer and an inorganic polymer. Alternatively, the substrate 10 may be formed of quartz, glass, or the like. A thickness of the substrate 10 may range from tens of μm to hundreds of μm. For example, a thickness of the substrate 10 may range from about 10 μm to about 500 μm, and more specifically, from about 200 μm to about 400 μm.

The first insulating layer 20 may be formed by depositing a nitride, for example, $Si_xN_y$, on the substrate 10. The first insulating layer 20 may be formed as a thin film or a thin layer, and a thickness of the first insulating layer 20 may be equal to or less than about tens of nm. In other words, a thickness of the first insulating layer 20 may range from about 10 nm to about 100 nm. The first insulating layer 20 may be formed by using CVD, for example, LPCVD or PECVD. If the first insulating layer 20 is formed by using LPCVD, the first insulating layer 21 may also be formed on the bottom surface of the substrate 10, and the first insulating layer 21 formed on the bottom surface of the substrate 10 is not shown in the remaining drawings.

Figure 4B:
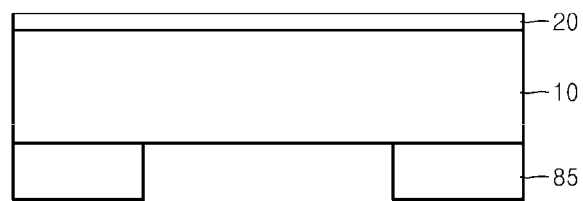

Referring to FIG. 4B, the mask layer 85 may be formed on the bottom surface of the substrate 10. The mask layer 85 may be formed of a nitride, for example, $Si_xN_y$. The mask layer 85 may be formed to a thickness of hundreds of nm, for example, from about 100 nm to about 500 nm. For example, the mask layer 85 may be formed by depositing $Si_xN_y$ on the bottom surface of the substrate 10 by using PECVD and patterning the $Si_xN_y$. The mask layer 85 may be formed by using dry etching, for example, RIE.

Figure 4C:
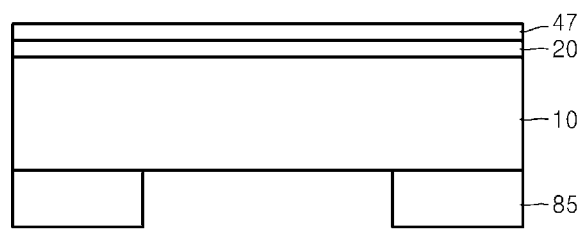

Referring to FIG. 4C, graphene 47 may be formed on the first insulating layer 20. The graphene 47 may be first formed on an auxiliary substrate by using CVD, mechanical or chemical exfoliation, epitaxial growth, or the like. The graphene 47 may be transferred from the auxiliary substrate to the first insulating layer 20. The auxiliary substrate may be formed of polydimehtylsiloxane (PDMS), polymethyl methacrylate (PMMA), or the like, and a thermally conductive tape may be used instead of the auxiliary substrate. The graphene 47 may include at least one graphene sheet. A thickness of the graphene 47 may be equal to or less than about 3.4 nm, and more specifically, may be equal to or less than about 1 nm. The graphene 47 may be formed by forming a catalyst layer formed of a metal on the first insulating layer 20 and being grown from the catalyst layer.

Figure 4D:
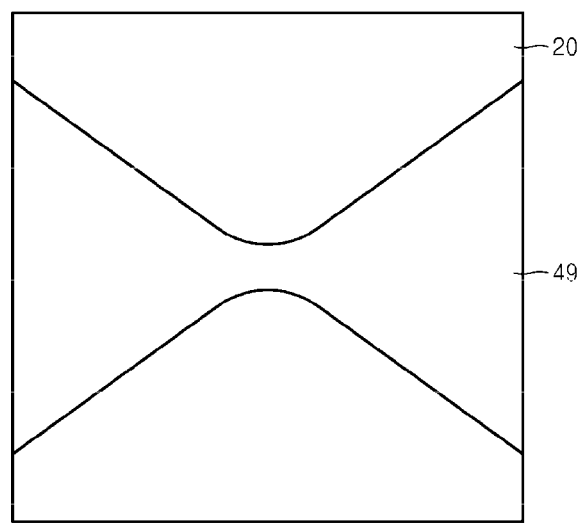

Referring to FIG. 4D, the graphene 47 may be patterned. The graphene 47 may be patterned by using photolithography. The graphene 47 may be etched by using oxygen plasma etching, to form graphene 49. A plane shape of the graphene 49 may be a bow tie. The graphene 49 may expose a portion of the first insulating layer 20 disposed under the graphene 49.

Figure 4E:
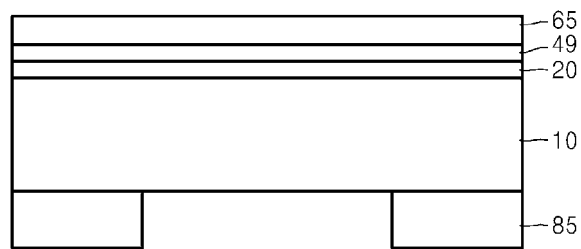

Referring to FIG. 4E, a sacrificial layer 65 may be formed on the first insulating layer 20 and the patterned graphene 49. The sacrificial layer 65 may be formed of an oxide, for example, a material selected from the group consisting of $SiO_2$, $Al_2O_3$, $TiO_2$, $BaTiO_3$, $PbTiO_3$, and a mixture thereof. If the sacrificial layer 65 is formed by using PECVD, the graphene 49 disposed under the sacrificial layer 65 may be damaged by plasma. Accordingly, the sacrificial layer 65 may be formed by using LPCVD. Also, the sacrificial layer 65 may be formed by using LPCVD at a low temperature equal to or lower than about 500° C., for example, from about 100° C. to about 500° C., and more specifically, from about 300° C. to about 500° C. In other words, the sacrificial layer 65 may be a low temperature oxide layer. A thickness of the sacrificial layer 65 may range from about 10 nm to about 500 nm, and more specifically, from about 50 nm to about 200 nm.

Figure 4F:
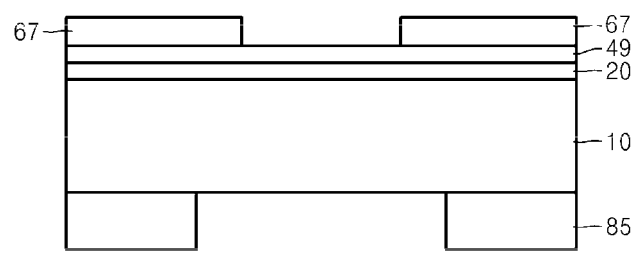

Referring to FIG. 4F, the sacrificial layer 65 may be patterned. A portion of the sacrificial layer 65 may be removed to expose a portion of the graphene 49 disposed under the sacrificial layer 65. Only a middle portion of the sacrificial layer 65 may be removed and edge portions of the sacrificial layer 65 may be left on both sides. The middle portion of the sacrificial layer 65 may be removed by using wet drying, for example, BOE. A sacrificial layer 67 may expose a middle portion and surroundings of the middle portion of the patterned graphene 49, that is, a middle portion and surroundings of the middle portion of the bow tie.

Figure 4G:
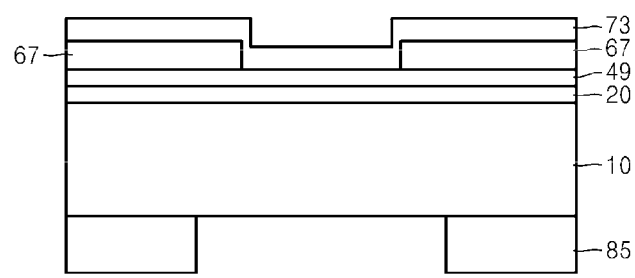

Referring to FIG. 4G, a second insulating layer 73 may be formed on the exposed portion of the graphene 49 and the sacrificial layer 67. The second insulating layer 73 may be formed by depositing a nitride, for example, $Si_xN_y$, on the sacrificial layer 67. The second insulating layer 73 may insulate the exposed portion of the graphene 49 by covering the exposed portion of the graphene 49. The second insulating layer 73 may be formed as a thin film or a thin layer, and a thickness of the second insulating layer 73 may be equal to or less than about tens of nm. In other words, a thickness of the second insulating layer 73 may range from about 10 nm to about 100 nm. Since the second insulating layer 73 is also formed on the exposed portion of the graphene 49, the second insulating layer 73 may not be formed by using PECVD, and may be formed by using, for example, LPCVD. Also, the second insulating layer 73 may be formed by using LPCVD at a high temperature equal to or higher than about 500° C., for example, from about 500° C. to about 1000° C.

Figure 4H:
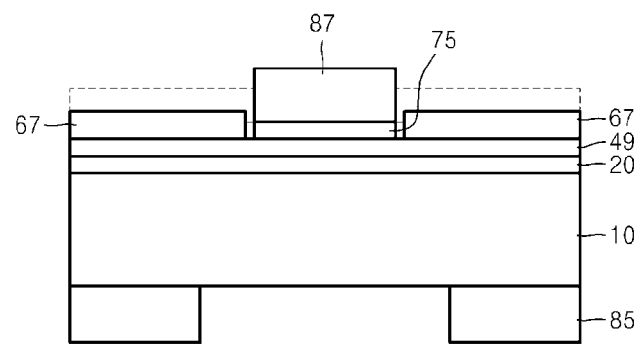

Referring to FIG. 4H, the second insulating layer 73 may be patterned. A portion of the second insulating layer 73 disposed on the sacrificial layer 67 may be removed. First, a photoresist layer 87 may be disposed on a remaining portion of the second insulating layer 73, and the second insulating layer 73 may be etched by using dry etching, for example, RIE. Then, the portion of the second insulating layer 73 on which the photoresist layer 87 is not disposed may be removed. Accordingly, both edge portions of the second insulating layer 73 may be etched to form a second insulating layer 75 under the photoresist layer 87. The second insulating layer 75 may cover the graphene 49 disposed under the second insulating layer 75, and may insulate the graphene 49.

Figure 4I:
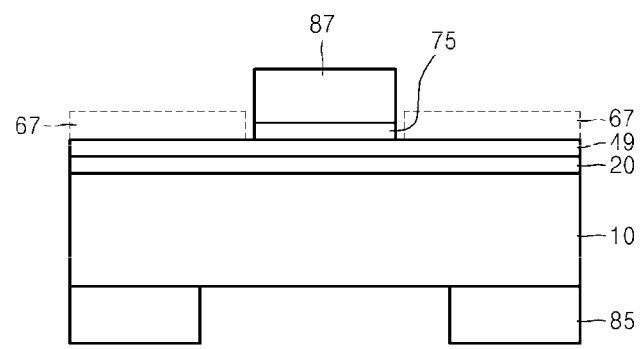

Referring to FIG. 4I, the sacrificial layer 67 may be removed. The sacrificial layer 67 may be removed by using wet etching, for example, BOE. Accordingly, an edge portion of the graphene 49 disposed under the sacrificial layer 67 may be exposed.

Figure 4J:
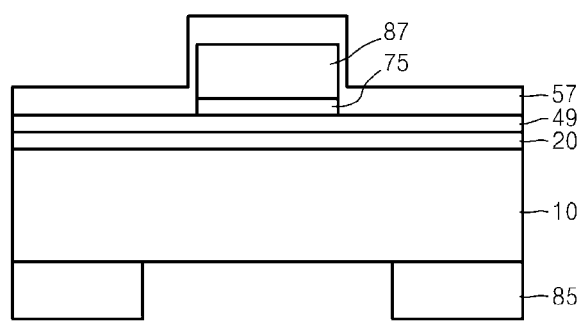

Referring to FIG. 4J, a metal layer 57 may be formed on the exposed edge portion of the graphene 49 and the photoresist layer 87. The metal layer 57 may be formed of a metal, for example, Au, Cr, Cu, Ni, Co, Fe, Ag, Al, Ti, Pd, or a mixture thereof. The metal layer 57 may be formed by depositing, for example, the above metals on the exposed edge portion of the graphene 49 and the photoresist layer 87.

Figure 4K:
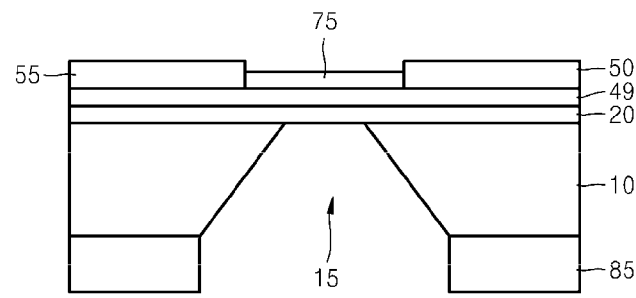

Referring to FIG. 4K, the photoresist layer 87 may be removed to form the first and second electrode pads 50 and 55, and the hole 15 may be formed in the substrate 10. If the photoresist layer 87 is lifted off, a portion of the metal layer 57 disposed on the photoresist layer 87 may be removed also. Accordingly, a remaining portion of the metal layer 57 may form the first and second electrode pads 50 and 55 which are spaced apart from each other. In the method of manufacturing the nanosensor 200, since the first and second electrode pads 50 and 55 each formed of a metal may melt in a high temperature process, the second insulating layer 75 may be first formed by using a high temperature process, for example, high-temperature LPCVD, before the first and second electrode pads 50 and 55 are formed by using the sacrificial layer 67.

The hole 15 may be formed by using wafer backside etching while shielding a front surface of the substrate 10. The hole 15 may be formed by using wet etching using the mask layer 85 as a hard mask. The hole 15 may be formed by using, for example, KOH etching. A diameter of the hole 15 may be equal to or less than tens of μm. For example, a diameter of the hole 15 may range from about 30 μm to about 490 μm, and more specifically, from about 60 μm to about 460 μm. The hole 15 may be formed by using selective etching, and may become narrower from the bottom surface of the substrate 10 toward the top surface of the substrate 10 on which the first insulating layer 20 is disposed. In other words, the hole 15 may be formed to have a tapered shape that becomes narrower from a lower portion toward an upper portion of the substrate 10.

Figure 4L:
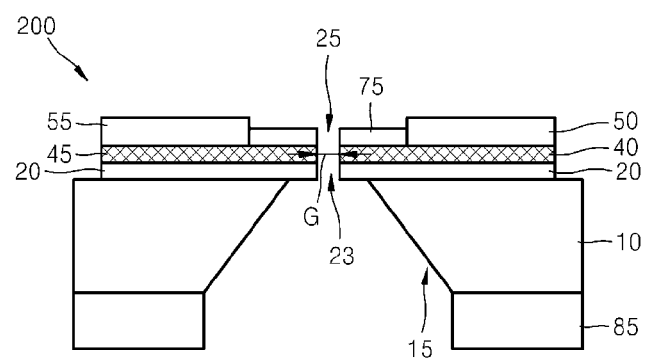

Referring to FIG. 4L, a nanopore may be formed in the first insulating layer 20, the graphene 49, and the second insulating layer 75. The nanopore may include the first nanopore 23 formed in the first insulating layer 20 and the second nanopore 25 formed in the second insulating layer 75. The first and second nanopores 23 and 25 may be simultaneously formed in the first insulating layer 20, the graphene 49, and the second insulating layer 75. Each of the first insulating layer 20 and the second insulating layer 75 may be formed of a nitride, and thus the first and second nanopores 23 and 25 may be easily formed. The first nanopore 23 may be connected to the hole 15 formed in the substrate 10. In other words, the first nanopore 23 may be formed in an area corresponding to the hole 15. A size of the first and second nanopores 23 and 25 may be determined according to a size of a target molecule to be detected or sequenced. A diameter of the first and second nanopores 23 and 25 may range from several nm to tens of nm. For example, a diameter of the first and second nanopores 23 and 25 may range from about 1 nm to about 100 nm, and more specifically, from about 2 nm to about 10 nm.

The first and second nanopores 23 and 25 may be formed by using, for example, TEM, SEM, or the like. More specifically, the first and second nanopores 23 and 25 may be formed by using an electron beam, a focused ion beam, a neutron beam, an X-ray, a y-ray, or the like. The graphene 49 may be divided into the first and second electrodes 40 and 45 due to the first and second nanopores 23 and 25 formed in the graphene 49.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A nanosensor comprising:
a substrate having a hole;
a first insulating layer disposed on the substrate and having a first nanopore at a location corresponding to the hole in the substrate;
first and second electrodes disposed on the first insulating layer, wherein the first and second electrodes are spaced apart from each other with the first nanopore positioned therebetween;
a first electrode pad disposed on a portion of the first electrode;
a second electrode pad disposed on a portion of the second electrode;
a protective layer, formed of an oxide, contacting at least a portion of the first and second electrode pads, and leaving a portion of the first and second electrodes exposed;
and a first portion of a second insulating layer contacting the protective layer and exposed portions of the first and second electrodes and a second portion of the second insulating layer spaced apart from the first and second electrodes, and wherein the second insulating layer is formed of a nitride, and wherein the first and second electrodes pads are disposed between the second portion of the second insulating layer and the first and second electrodes, respectively.

2. The nanosensor of claim 1, wherein the protective layer covers only a portion of each of the first and second electrode pads, and the first and second electrode pads cover only a portion of the first and second electrodes, respectively.

3. The nanosensor of claim 1, wherein the second insulating layer has a second nanopore connected to the first nanopore.

4. The nanosensor of claim 1, wherein the exposed portions of the first and second electrodes are adjacent the nanopore.

5. The nanosensor of claim 1, wherein the first and second electrodes comprise graphene or carbon nanotubes.

* * * * *